United States Patent [19]
Dragotta

[11] Patent Number: 5,444,540
[45] Date of Patent: Aug. 22, 1995

[54] BLACK BACKGROUND INSPECTION APPARATUS

[75] Inventor: Peter J. Dragotta, Wayne, N.J.

[73] Assignee: M. W. Technologies, Inc., Elmwood Park, N.J.

[21] Appl. No.: 229,159

[22] Filed: Apr. 18, 1994

[51] Int. Cl.$^6$ ............................................. G01N 21/90
[52] U.S. Cl. ...................................... 356/427; 356/240
[58] Field of Search ............... 356/240, 427; 359/601, 359/614

[56] References Cited

U.S. PATENT DOCUMENTS

| | | |
|---|---|---|
| 2,646,715 | 7/1953 | Stout et al. . |
| 3,257,507 | 6/1966 | Borberg et al. ...................... 359/601 |
| 3,863,763 | 2/1975 | Kollár et al. . |
| 4,676,650 | 6/1987 | Bjorndal et al. ...................... 356/427 |
| 5,261,546 | 11/1993 | Van Der Grift ................ 356/427 X |

Primary Examiner—Vincent P. McGraw
Assistant Examiner—K. P. Hantis
Attorney, Agent, or Firm—Anthony J. Casella; Gerald E. Hespos

[57] ABSTRACT

An inspection apparatus is provided for accurate identification of particulates in parenteral drugs. The inspecting apparatus includes a black inspection panel having an aperture extending therethrough. A light-tight enclosure surrounds the aperture in the panel on the side of the panel opposite the side on which the parenteral drug is inspected. Interior surfaces of the enclosure have black surfaces with finishes to achieve low light reflection. The combination of the aperture and the black enclosure provides enhanced blackness that is not likely to be affected by dust, dirt or surface damages. Hence, greater accuracy and reliability in black background particulate inspection is achieved.

19 Claims, 2 Drawing Sheets

BLACK BACKGROUND INSPECTION APPARATUS

BACKGROUND OF THE INVENTION

1. Field of the Invention

The subject invention relates to an apparatus having an improved black background to enable enhanced visual inspection for particulate matter in parenteral drugs. The black background also can be used to improve accuracy of any optical measuring device using photocells or any automatic vision system where an object is surface illuminated and inspected against a dark background for contrast.

2. Description of the Prior Art

Parenteral drugs are subject to carefully controlled manufacturing processees and post-manufacturing inspection processees to ensure suitability for their intended purpose. One such post-manufacturing process involves a visual inspection for particulates suspended in the drug. These particulates can originate in the drug manufacturing process, in the process of manufacturing vials, ampules or syringes or in the filling process of such vials, ampules or syringes. Particulates that might exist typically are small and can be virtually any shape or color.

The prior art typically relies upon visual inspection of a statistically significant sample of containers (e.g. vials, ampules or syringes) filled with carefully identified batches of parenteral drugs and their containers. Visual observation of unacceptable particulates in the parenteral drugs typically will result in an entire batch being subject to more extensive inspection and the entire batch may be discarded if the initial tests are accurate. A bad batch could generate a subsequent inquiry to identify the source of the particulate in the tightly controlled manufacturing process.

The typical prior art particulate inspection apparatus includes a black inspection background and a white inspection background. The vial, ampule or syringe is placed between the inspector and the black inspection background to identify any light colored particles that may be suspended in the drug. The container is then moved between the inspector the white inspection background to enable the inspector to see dark particulate matter that may be suspended in the drug. The inspector often may be aided by a magnifying glass or other focusing means positioned between the inspector and the container of parenteral drugs being inspected.

The accuracy and reliability of the prior art particulate inspection apparatus depends in part upon the whiteness and blackness of the backgrounds used for the inspection. For example, dirt or dust on the white or black background may appear as a particle suspended in a parenteral drug. Scratches or other damage that will inevitably occur during use also are visually apparent through the parenteral drug, and may be perceived as particulate matter that is actually not present. Similarly, over time, the reflectivity and color of the black or white surfaces can change. Any or all of the above deficiencies in the blackness and/or whiteness of the respective backgrounds can cause a higher-than-necessary reject rate of drugs, with very substantial cost penalties to the pharmaceutical manufacturer. More particularly, the pharmaceutical manufacturer will have already invested significant amounts of time and money in an entire batch of drugs and a corresponding batch of ampules, vials or syringes when the suspected particulate matter is observed. The entire batch will then have to be isolated and either discarded or subjected to much more extensive testing and inspection.

Accordingly, it is an object of the subject invention to provide an apparatus to achieve enhanced particulate inspection.

It is another object of the subject invention to provide a particulate inspection apparatus having a black background that will retain a high degree of blackness for a very long time.

It is a further object of the subject invention to provide a black background for particulate inspection apparatus that is not significantly affected by dust or dirt, that is not easily damaged and that is not affected by changes in coloration or reflectivity over time.

SUMMARY OF THE INVENTION

The subject invention is directed to an apparatus providing an enhanced black background for particulate inspection of parenteral drugs or other objects. The apparatus comprises a black inspection panel having a black front surface, a rear surface and an aperture extending therethrough. The aperture preferably is dimensioned to be larger than any of the drug containers or other objects to be inspected. The black inspection panel with the aperture may be generally planar and may have a black front surface that is durable and cleanable.

The apparatus further comprises an enclosure disposed on the rear surface of the black panel which is opposite the side on which the container of drugs will be positioned for inspection. The enclosure has cross-sectional dimensions which exceed the dimensions of the aperture through the black inspection panel, such that the enclosure completely surrounds the aperture. Walls defining the enclosure are formed from a material having a black inwardly facing surface that will minimize light reflection. The walls defining the enclosure can be formed entirely from flat black plastic with black coloration throughout. Alternatively, the walls defining the enclosure can be formed from any convenient substrate material having an appropriate flat black coating applied thereto. As explained further below, a black flocking material is effective for minimizing light reflection. However, various flat black paints or black plastic with a matte or flat finish are effective. The mounting of the enclosure to the back of the black inspection panel preferably is light-tight to prevent ambient light from passing between the black inspection panel and the enclosure.

The apparatus may further comprise a light source spaced from the black front surface of the black inspection panel. The light source preferably is operable to direct a narrow plane of light parallel to the black inspection panel and generally in line with the aperture through the black inspection panel.

The apparatus of the subject invention may also comprise automatic electro-optical inspection means spaced from the front side of the black inspection panel. The electro-optical inspection means may comprise at least one light source and/or at least one light detector for detecting particulate matter or other characteristics of an object being inspected.

The apparatus of the subject invention is used by merely placing the container of parenteral drugs or other objects to be inspected between the aperture in the black panel and either the human inspector or the electro-optical inspection means. The black enclosure surrounding the aperture provides an exceptionally high degree of blackness that enables accurate identification of relatively light colored particulates suspended in the parenteral drug. Additionally, the high degree of blackness achieved with the subject invention enables a very high contrast relative to an object being inspected by a photodetector or vision system using a pixel count to define the size and shape of the object being inspected. The effective black hole provided by the subject apparatus is not likely to be damaged, and is substantially less affected by dirt or discoloration as compared to the above described continuous prior art black panel.

The black background of the subject apparatus may be used in proximity to a white inspection panel, such as the conventional white background described above. Additionally, the subject particulate inspection apparatus can be used in combination with magnifying or focusing means to enhance the visual observation.

DETAILED DESCRIPTION OF THE PREFERRED EMBODIMENT

Figure 1:
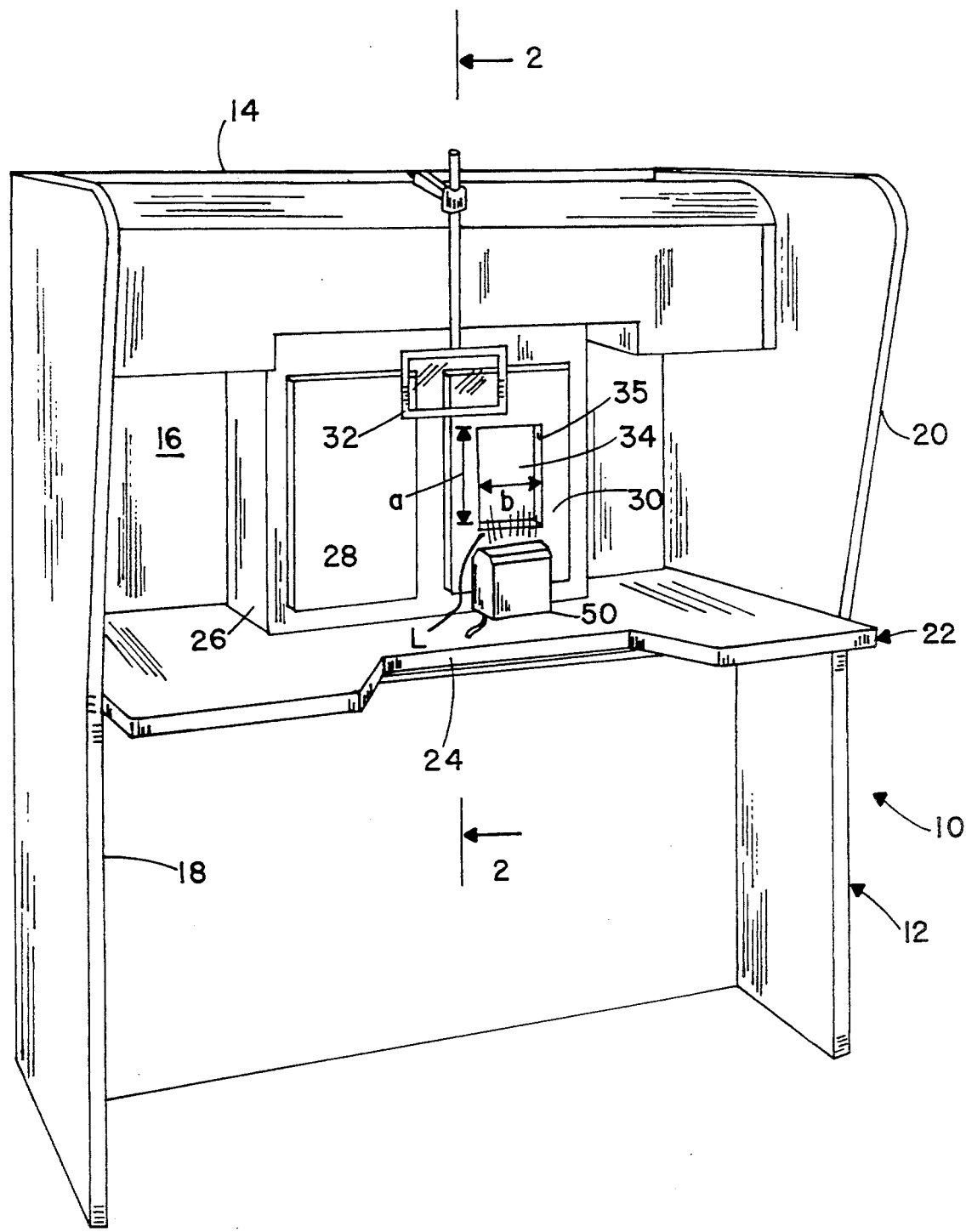
FIG. 1 is a perspective view of an apparatus in accordance with the subject invention.

The apparatus of the subject invention is identified generally by the numeral 10 in FIG. 1. The apparatus 10 includes a support frame 12 having a substantially vertical rear wall 14 with a front face 16. Side walls 18 and 20 extend generally parallel to one another and project forwardly from the front face 16 of the rear wall 14 to define a partial enclosure for an inspector. A generally horizontal work table 22 extends forwardly from the front face 16 of the rear wall 14 and is partly supported by the side walls 18 and 20 of the support frame 12. In the preferred embodiment, as illustrated in FIG. 1, the horizontal table 22 includes a recessed front edge 24 to accommodate the inspector in the area where particulate inspection is to be undertaken.

An inspection panel support 26 projects forwardly from the front face 16 of the rear wall 14, and supports substantially adjacent white and black inspection panels 28 and 30 respectively for performing white and black background particulate inspection. A magnifier 32 is adjustably mounted forwardly of the rear wall 14 and rearwardly of the front edge 26 of the work table 24 at a position generally registered with the white and black inspection panels 28 and 30. As in the prior art, the magnifier 32 is provided for improved visual inspection. The white inspection panel 28 is substantially planar and has a durable white finish that can readily be cleaned. White background panels used in prior art particulate inspection apparatus are acceptable.

The black inspection panel 30 also is generally planar and also has a durable black finish that can readily be cleaned. Unlike the white panel 28, however, the black panel 30 has an aperture 34 formed therethrough. The aperture 34 has height and width dimensions "a" and "b" that exceed the largest dimension of a vial, ampule, syringe or other such drug containers that are likely to be inspected. Edge regions 35 of the aperture 34 also are black. The black edges 35 can be achieved either by using an appropriate coating material or by forming the panel from a black plastic that is of uniform color throughout.

Figure 2:
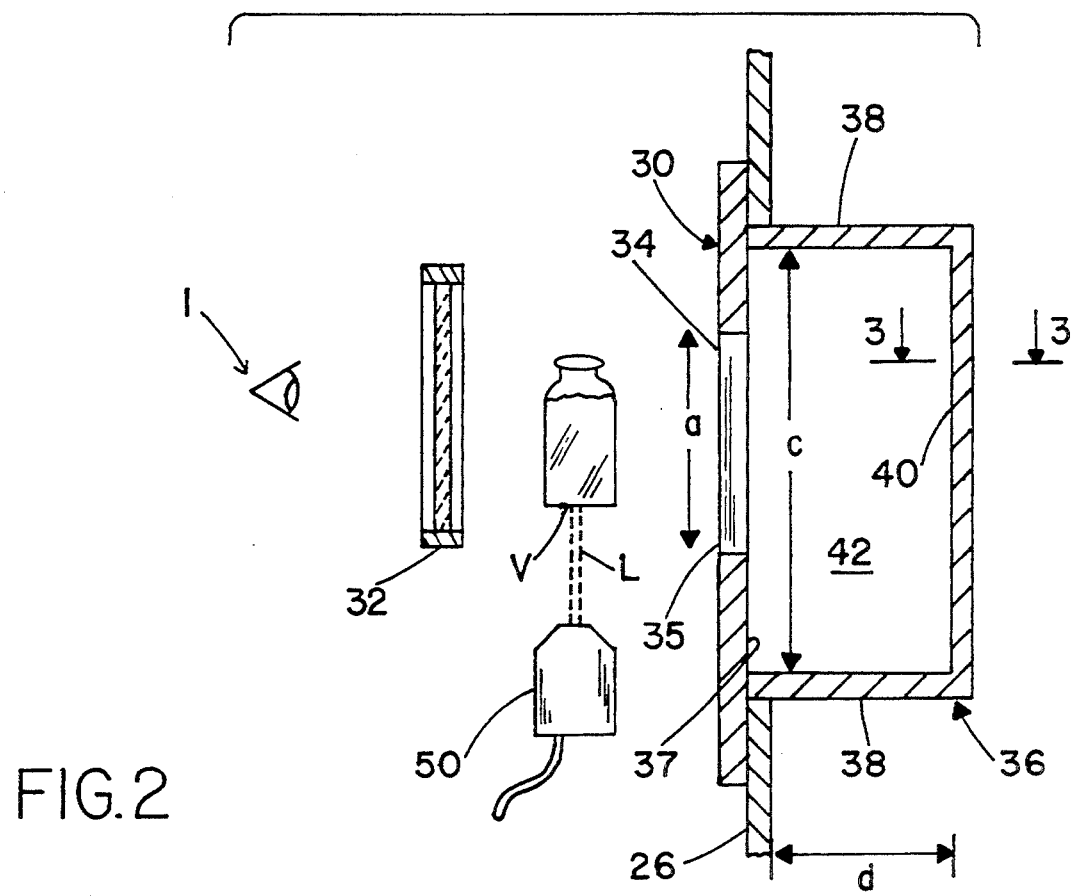
FIG. 2 is a cross-sectional view taken along line 2—2 in FIG. 1, and also showing a vial and an inspector.

With reference to FIG. 2, an enclosure 36 is securely mounted to the rear side 37 of the black inspection panel 30 to surround the aperture 34. The enclosure 36 includes a plurality of side walls 38 which are aligned generally perpendicular to the black inspection panel 30 and a rear wall 40 which is generally parallel to the black inspection panel 30. As depicted in FIG. 2, the side walls 38 of the enclosure 36 are securely mounted directly to the rear side 37 of the black inspection panel 30 in a light-tight manner to minimize the amount of ambient light entering the enclosure 36. This construction enables the combination of the black inspection panel 30 and the enclosure 36 to be removed from the inspection panel support 26 for repair or replacement if necessary. In an alternate construction, the enclosure 36 may be mounted to the rear face of the inspection panel support 26, while the black inspection panel 30 may be mounted to the front face of the inspection panel support 26. With this latter construction, the enclosure 36 and the black inspection panel 30 cooperate with one another, but are not directly in contact.

Figure 3:
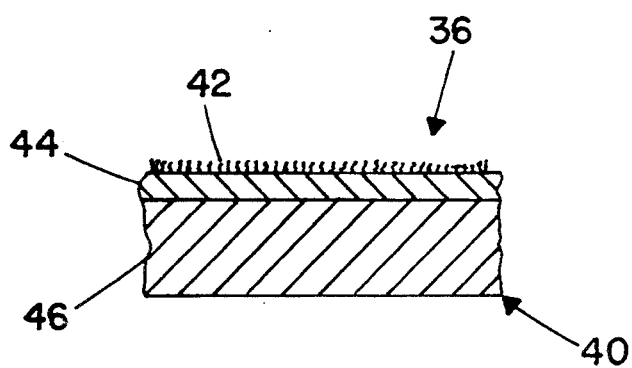
FIG. 3 is a cross-sectional view taken along line 3—3 in FIG. 2.

The side walls 38 and rear wall 40 of the enclosure 36 define a black interior surface 42 having surface characteristics that will prevent or minimize light reflection. In this regard, the interior surface 42 of the enclosure 36 may be defined by a black flocking 44, such as felt, that is applied to a substrate 46 as shown in FIG. 3. Alternatively, a black contact material or a black flat paint having appropriate light reflection characteristics may be used in place of flocking 44 on the substrate 46 shown in FIG. 3. In still other embodiments, the walls 38, 40 of the enclosure 36 may be defined by unitary plastic panels of uniform black color throughout.

Returning to FIG. 2, the enclosure 36 defines a height "c" and a width (not shown) which exceed the corresponding height "a" and width "b" of the aperture 34 in the black panel 30. Additionally, the enclosure 36 preferably defines a depth "d". The height "c", depth "d" and width preferably are selected to ensure that a human inspector "I" or comparably positioned electro-optical detector will align a vial "V" or other such container to be inspected with the rear wall 40 and not the side walls 38 of the enclosure 36. These relative dimensions will prevent a variation in the background coloration and shading due to different angular alignments of the intersecting surfaces within the enclosure 36.

The apparatus 10 further includes a light source 50 for directing a narrow plane of light "L" parallel to the black inspection panel 30 at a location in line with the aperture 34.

The apparatus 10 is employed to perform the white background particulate inspection by using the white inspection panel 28 in substantially the conventional manner. The black background particulate inspection is carried out by placing the vial "V" or other such container of parenteral drugs to be inspected at a location between the inspector "I" (or the comparably positioned electro-optical detector) and the aperture 34 in the black inspection panel 30, such that the narrow plane of light "L" projects into the vial "V". Thus, the inspector "I" or electro-optical detector will be viewing the parenteral drug against the black background defined by the enclosure 36. Interior surfaces 42 of the enclosure 36 are not subject to excessive accumulation of dirt or debris, and are substantially less likely to be damaged by inadvertent contact during use. Additionally, interior surfaces 42 of the enclosure 36 will remain substantially dark at all times, and hence will be less likely to fade or be subject to other discoloration. The effective black hole created by the combination of the aperture 34 in the panel 30 and the light-tight enclosure 36 surrounding the aperture 34 provides a very black background that enables enhanced accuracy in the black background particulate inspection of parenteral drugs. Substantially fewer false indications of particulates will result and improved identification of actual particulates will be achieved.

While the invention has been described with respect to a preferred embodiment, it is apparent that various changes can be made without departing from the scope of the invention. For example, the above described black background for particulate inspection can be used entirely independently of a white background. The black background also can be used in combination with automated feed means for delivering parenteral drugs to be inspected, and the schematically illustrated inspector "I" can be an electro-optical inspection means, such as a photo-detector or vision system. Additionally, the invention is not limited to drug inspection systems, but is suitable for any photodetector or vision system where a high contrast relative to an object's boundary is desirable, such as systems using a pixel count to define the size and shape of the product to be inspected. These and other variations will be apparent to persons skilled in this art after having read the preceding disclosure.

I claim:

1. A black background inspection apparatus comprising: an inspection station for positioning an article to be inspected; an observation station spaced from said inspection station for optically observing the article to be inspected, and an inspection panel having a black front surface, an opposed rear surface and an aperture extending through said inspection panel from said front surface to said rear surface, said inspection panel being disposed such that said black front surface of said inspection panel faces said inspection station and such that said inspection station is intermediate said observation station and said inspection panel, an enclosure disposed in light-tight engagement adjacent said rear surface and surrounding said aperture, said enclosure having black interior surfaces for substantially preventing light reflection in said enclosure, whereby objects to be inspected can be placed at said inspection station and in proximity to said aperture and observed from said observation station against the black interior surfaces of said enclosure.

2. An apparatus as in claim 1, wherein said enclosure comprises a plurality of walls having substrates, said black interior surfaces of said enclosure being defined by a black material applied to said substrate.

3. An apparatus as in claim 2, wherein the black material is a black flocking.

4. An apparatus as in claim 2, wherein the black material is a black plastic contact sheet material adhered to the substrate.

5. An apparatus as in claim 2, wherein the black material is a flat black paint applied to the substrate.

6. An apparatus as in claim 1, wherein said enclosure is formed from black plastic material of uniform black color throughout.

7. An apparatus as in claim 1, wherein the front face of the inspection panel is black.

8. An apparatus as in claim 7, wherein said aperture through said inspection panel defines at least one edge, said edge being black.

9. An apparatus as in claim 1, wherein said enclosure is secured directly to the rear side of said inspection panel.

10. An apparatus as in claim 1, wherein said objects to be inspected are containers of parental drugs, said aperture in said inspection panel defining cross-sectional dimensions greater than dimensions of said containers of parental drugs.

11. An apparatus as in claim 1, wherein said enclosure comprises a plurality of side walls extending generally perpendicular to said inspection panel and a rear wall extending generally parallel to said inspection panel, said aperture and said enclosure being dimensioned such that said side walls of said enclosure are not readily visible through said aperture.

12. An apparatus as in claim 1, further comprising a white inspection panel adjacent to said panel having said aperture therein.

13. An apparatus as in claim 1, wherein said observation station further comprises light focusing means adjustably mounted for disposition such that said object being inspected at said inspection station can be placed intermediate said light focusing means and said aperture in said inspection panel.

14. An apparatus as in claim 1, wherein said inspection station comprises a light source for directing a narrow plane of light parallel to said front surface of said inspection panel and in line with the aperture through said inspection panel.

15. An apparatus for particulate inspection of parenteral drugs disposed in substantially transparent containers, said apparatus comprising: an inspection station for receiving said containers of drugs, an observation station adjacent said inspection station for optically observing said containers of drugs, a continuous white inspection panel and a black inspection panel disposed such that said inspection station is intermediate said observation station and said inspection panels, each said inspection panel having a front surface facing the inspection station and said black inspection panel having a rear surface facing away from said inspection station, an aperture extending through said black inspection panel from said front surface to said rear surface thereof, said aperture being larger than the container of drugs being inspected, an enclosure mounted in light-tight relationship to said rear surface of said black inspection panel and surrounding said aperture in said black inspection panel, said enclosure defining interior surfaces, said interior surfaces being black and having surface texture for substantially preventing reflection of light, whereby disposition of said container of parenteral drugs in said inspection station and in alignment with said aperture provides a black background for accurate and reliable inspection of particulates in said drug.

16. An apparatus as in claim 15, wherein said enclosure comprises a substrate, and wherein said black interior of said enclosure is defined by a black coating applied to said substrate.

17. An apparatus as in claim 16, wherein said coating is defined by black flocking.

18. An apparatus for conducting a black-background inspection of an object, said apparatus comprising:

an inspection panel having a black front surface, an opposed rear surface and an aperture extending through said inspection panel from said front surface to said rear surface, an enclosure disposed in light-tight engagement at said rear surface of said inspection panel and surrounding said aperture, said enclosure having flat black interior surfaces for substantially preventing light reflection in said enclosure;

an observation station spaced from said inspection panel such that said front surface of said inspection panel faces said observation station;

an object inspection station defined between said observation station and said front of said inspection panel and substantially registered with the aperture through the inspection panel;

light generating means in said observation station and in front of said inspection panel for directing light toward the object inspection station; and optical means disposed in register with said aperture through said inspection panel such that said object inspection station is intermediate said aperture and said optical means, said optical means being for receiving light from said source and reflected from said object for enabling evaluation thereof.

19. An apparatus as in claim 18, wherein the optical means comprises light focusing means.

* * * * *